United States Patent [19]
Grohman

[11] Patent Number: 5,494,052
[45] Date of Patent: Feb. 27, 1996

[54] GARMENT-TYPE PERSONNEL RESTRAINT APPARATUS

[76] Inventor: Sylvia J. Grohman, 5234 Colebrook, San Antonio, Tex. 78228

[21] Appl. No.: 393,669
[22] Filed: Feb. 24, 1995
[51] Int. Cl.⁶ .................................................. A61F 5/37
[52] U.S. Cl. .................................. 128/873; 128/876
[58] Field of Search ................................ 128/845, 846, 128/869–876, DIG. 15; 602/19; 269/484, 485, DIG. 6

[56] References Cited

U.S. PATENT DOCUMENTS

| | | |
|---|---|---|
| D. 315,993 | 4/1991 | Wenderoth . |
| 2,456,898 | 12/1948 | Strandhagen ........................... 128/870 |
| 2,495,482 | 1/1950 | Rogatz ................................... 128/876 |
| 4,165,123 | 8/1979 | Hutson . |
| 4,657,005 | 4/1987 | Williamson ............................ 128/875 |
| 4,672,958 | 6/1987 | Garman ................................. 128/873 |
| 4,697,849 | 10/1987 | Smith . |
| 4,795,176 | 1/1989 | Harrigan ............................... 128/873 |
| 4,911,105 | 3/1990 | Hocum .................................. 128/876 |
| 5,141,286 | 8/1992 | Ayala, Jr. et al. . |
| 5,232,267 | 8/1993 | DeMatteo et al. . |
| 5,256,135 | 10/1993 | Avihod .................................. 128/874 |
| 5,400,803 | 3/1995 | Vines ..................................... 128/869 |

Primary Examiner—Michael A. Brown

[57] ABSTRACT

A garment-type personnel restraint apparatus secures a person to a chair and includes a garment assembly adapted to be worn by the person and a strap assembly that is connected to the chair. The garment assembly includes a front portion, a middle portion, and a rear portion. The garment assembly includes a connector assembly located on an outer surface of the garment assembly. The strap assembly includes a strap connection assembly adapted to connect to the outer-surface garment connector assembly when the garment assembly is worn by a person and when the strap assembly is affixed to the chair. The strap assembly includes a strap array which encompasses either the seat portion or the back portion of the chair. When the strap assembly encompasses the seat portion of the chair, both the outer-surface garment connector assembly of the garment assembly and the strap connection assembly of the strap assembly are located adjacent to the seat portion of the chair. Alternatively, when the strap assembly encompasses the back portion of the chair, both the outer-surface garment connector assembly and the strap connection assembly are located adjacent to the back portion of the chair.

9 Claims, 4 Drawing Sheets

GARMENT-TYPE PERSONNEL RESTRAINT APPARATUS

BACKGROUND OF THE INVENTION

1. Field of the Invention

The present invention relates generally to personnel restraints and, more particularly, to personnel restraints especially adapted for restraining a person in a chair.

2. Description of the Prior Art

When small children sit in high chairs, they often have a tendency to slip off of the seat portion of the high chair. Of course, such an occurrence can be hazardous to the child and frightening to a provider of child care, be it a parent, a baby sitter, or a person at a child day care center, hospital, or anywhere small children are cared for.

Throughout the years, a number of innovations have been developed relating to restraining children in high chairs, and the following U.S. patents are representative of some of those innovations: U.S. Pat. No. 4,697,849; 5,141,286; and 5,232,267. More specifically, U.S. Pat. No. 4,697,849 discloses a child's high chair restraining device which employs leg straps that connect directly to a child's thighs. Such a device may impede the child's leg movement which in the high chair. In this respect, it would be desirable if a high chair child restraint device were provided which does not impede a child's leg movement when the child is seated in the high chair.

U.S. Pat. No. 5,141,286 discloses a high chair baby seat which employs a wooden dowel that is placed under a child's legs as the child is seated in the high chair. This device also can impede leg motion of the child that is seated in the high chair. Moreover, over time, the wooden dow may splinter and require maintenance or replacement to continue its safe use. In this respect, it would be desirable if a high chair child restraint device were provided which does not employ wood.

U.S. Pat. No. 5,232,267 discloses high chair safety pants which have hook or loop material which attaches to complementary loop or hook material that is attached to the top surface of the seat of the high chair. To remove a child from a high chair with which this device is employed may require a three-handed operation. That is, more than two people may need to be available. One person may need to use two hands to firmly grasp the child. A second person may need to pull on the pants to separate the hook or loop material of pants from the complementary loop or hook material on the seat. If a second person is not employed, the child may be pulled out of the pants with the pants being left attached to the seat of the high chair. In this respect, it would be desirable if a high chair child restraint device were provided which enables a child to be removed from the seat of the high chair with a two-handed operation.

In addition, the following U.S. patents may be of interest for their disclosure of additional innovations relating to high chairs: U.S. Pat. No. 4,165,123, and Des. 315,993.

Children in high chairs are not the only persons that sometimes should be restrained in chair seats. For example, sometimes adult patients suffer from debilitating injuries or incapacities and should be restrained in a chair seat. Reasons for restraining an adult person in a chair seat include maintaining good posture, preventing the person from tilting forward, preventing the person from tilting from side to side, and preventing the person from slipping off of the seat of the chair.

Still other features would be desirable in a garment-type personnel restraint apparatus. Aside from restraining a person in a seat, it may be desirable for a restraint device to protect a person's chest area from food or other soiling material. In other words, it would be desirable if a personnel restraint device were provided an apron-like portion for protecting a person's chest from soiling materials.

For maintaining good posture, for preventing a person from tilting forward while seated in a chair, and for preventing the person from tilting from side to side while seated in the chair, it would be desirable if a personnel restraint device had a portion for connecting the person's torso to the vertically oriented back of the chair.

Thus, while the foregoing body of prior art indicates it to be well known to use personnel restraints with chairs, the prior art described above does not teach or suggest a garment-type personnel restraint apparatus which has the following combination of desirable features: (1) does not impede a child's leg movement when the child is seated in a high chair; (2) does not employ wood; (3) enables a child to be removed from the seat of a high chair with a two-handed operation; (4) provides an apron-like portion for protecting a person's chest from materials that soil clothing; and (5) has a portion for connecting the person's torso to the vertically oriented back of a chair. The foregoing desired characteristics are provided by the unique garment-type personnel restraint apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a garment-type personnel restraint apparatus which secures a person to a chair which has a seat portion and a back portion extending upward from the seat portion. The garment-type personnel restraint apparatus includes a garment assembly adapted to be worn by the person. The garment assembly includes a front portion, a middle portion, and a rear portion. The garment assembly includes a connector assembly located on an outer surface of the garment assembly. A strap assembly includes a strap connection assembly adapted to connect to the outer-surface garment connector assembly. The strap assembly includes a strap array which encompasses either the seat portion or the back portion of the chair.

The strap array of the strap assembly may include at least one strap portion which has a sufficient strap length for encompassing either the seat portion or the back portion of the chair. The at least one strap portion includes a first end connector and a second end connector adapted to connect with the first end connector when the at least one strap portion encompasses either the seat portion or the back portion of the chair.

The front portion and the rear portion may have at least a first width. The middle portion has a second width, and the first width is greater than the second width. The front portion includes two front corner portions which include front connectors. The rear portion includes two rear corner portions which include rear connectors which are complementary to the front connectors. The middle portion includes a middle connector assembly located on a bottom surface of the garment assembly.

The strap assembly includes a strap connection assembly adapted to connect to the middle connector assembly of the garment assembly. The strap assembly may include at least one strap portion which has a sufficient strap length for encompassing the seat portion of the chair. The at least one strap portion includes a first end connector and a second end connector adapted to connect with each other when the at least one strap portion encompasses the seat portion of the chair.

The front connectors includes first hook or loop connectors, and the complementary rear connectors includes second loop or hook connectors to the first hook or loop connectors. The middle connector assembly includes a quantity of middle-connector hook or loop connectors, and the strap connection assembly includes a quantity of strap-connector loop or hook connectors which are complementary to the middle-connector hook or loop connectors.

The strap assembly includes a second strap portion connected at right angles to the strap portion. The second strap portion has a sufficient strap length for encompassing the seat portion of the chair. The second strap portion includes a first end connector and a second end connector adapted to connect with each other when the second strap portion encompasses the seat portion of the chair.

The front portion of the garment assembly includes a two-strap belt assembly adapted to encircle a person's waist. The two-strap belt assembly includes a first end connector and a second end connector adapted to connect together when the two-strap belt assembly encircles the person's waist. The rear portion of the garment assembly includes a back-coveting portion connected to the middle portion of the garment assembly. A shoulder-covering portion is connected to the back-covering portion, and a torso-coveting portion is connected to the shoulder-coveting portion. The back-coveting portion of the rear portion of the garment assembly includes a back-located connector assembly located on an outer surface of the back-covering portion. The shoulder-covering portion of the rear portion of the garment assembly includes an aperture adapted to fit over a head and a neck of a person and includes shoulder strap portions adjacent to the aperture, and the torso-covering portion includes an apron portion and strap assemblies which extend laterally from the apron portion. The strap assemblies include strap connectors that are adapted to connect with complementary receiver connectors that are located on the back-coveting portion of the rear portion of the garment assembly.

The strap assembly includes a strap array for encompassing the back portion of the chair. A back-covering portion is connected between the strap array, and a back-covering-portion-mounted connector assembly located on the back-covering portion adapted for connection to the back-located connector assembly of the garment assembly. The strap array includes a front portion, a middle portion connected to the front portion, and a rear portion connected to the middle portion. The front portion of the strap array includes a plurality of strap assemblies which project laterally from the front portion. The strap assemblies include connector-carrying ends. The rear portion of the strap array includes connector portions which are complementary to the connector-carrying ends of the strap assemblies.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved garment-type personnel restraint apparatus which has all of the advantages of the prior art and none of the disadvantages.

It is another object of the present invention to provide a new and improved garment-type personnel restraint apparatus which may be easily and efficiently manufactured and marketed.

It is a further object of the present invention to provide a new and improved garment-type personnel restraint apparatus which is of durable and reliable construction.

An even further object of the present invention is to provide a new and improved garment-type personnel restraint apparatus which is susceptible of a low cost of manufacture with regard to both materials and labor, and which accordingly is then susceptible of low prices of sale to the consuming public, thereby making such garment-type personnel restraint apparatus available to the buying public.

Still yet a further object of the present invention is to provide a new and improved garment-type personnel restraint apparatus which does not impede a child's leg movement when the child is seated in a high chair.

Still another object of the present invention is to provide a new and improved garment-type personnel restraint apparatus that does not employ wood.

Yet another object of the present invention is to provide a new and improved garment-type personnel restraint apparatus which enables a child to be removed from the seat of a high chair with a two-handed operation.

Even another object of the present invention is to provide a new and improved garment-type personnel restraint apparatus that provides an apron-like portion for protecting a person's chest from materials that soil clothing.

Still a further object of the present invention is to provide a new and improved garment-type personnel restraint apparatus which has a portion for connecting the person's torso to the vertically oriented back of a chair.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

With reference to the drawings, a new and improved garment-type personnel restraint apparatus embodying the principles and concepts of the present invention will be described.

Turning to FIGS. 1–4, there is shown a first embodiment of the garment-type personnel restraint apparatus of the invention generally designated by reference numeral 10. More specifically, the garment-type personnel restraint apparatus 10 secures a person 12 to or restrains a person in a chair 14 which has a seat portion 16 and a back portion 18 extending upward from the seat portion 16. The garment-type personnel restraint apparatus 10 includes a garment assembly 20 adapted to be worn by the person 12. The garment assembly 20 includes a front portion 22, a middle portion 24, and a rear portion 26. The garment assembly 20 includes a connector assembly located on an outer surface of the garment assembly 20. A strap assembly 40 includes a strap connection assembly adapted to connect to the outer-surface garment connector assembly. The strap assembly 40 includes a strap array which encompasses either the seat portion 16 or the back portion 18 of the chair 14.

The strap array of the strap assembly 40 may include at least one strap portion 52 which has a sufficient strap length 54 for encompassing either the seat portion 16 or the back portion 18 of the chair 14. The at least one strap portion 52 includes a first end connector 56 and a second end connector 58 adapted to connect with the first end connector 56 when the at least one strap portion 52 encompasses either the seat portion 16 or the back portion 18 of the chair 14.

Figures 3, 4:
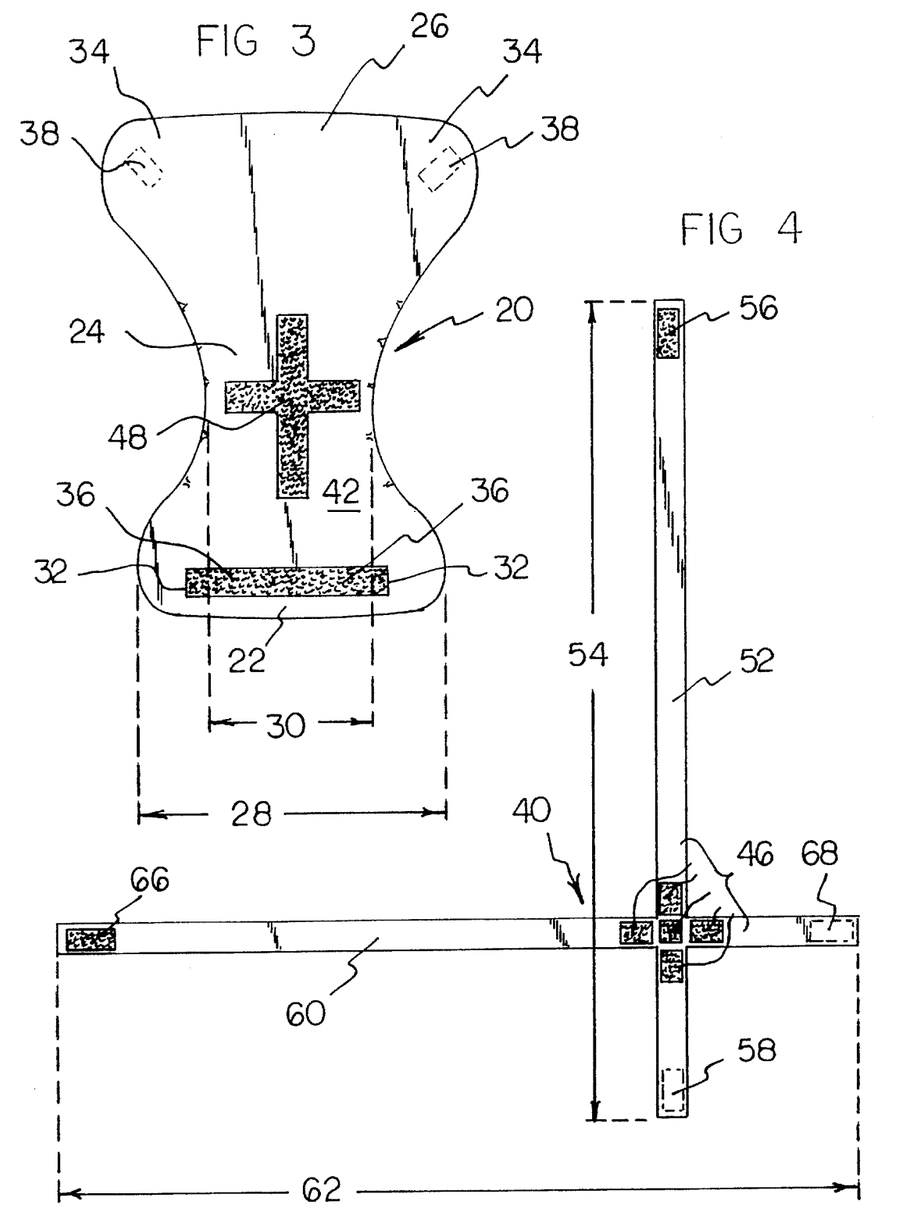
FIG. 3 is a bottom view of a pants portion of the embodiment of the invention shown in FIG. 2 with the pants portion in a flat, open orientation.
FIG. 4 is a top view of a strap portion of the embodiment of the invention shown in FIG. 2 with the strap portion in a flat, open orientation.

The front portion 22 and the rear portion 26 may have at least a first width 28. The middle portion 24 has a second width 30, and the first width 28 is greater than the second width 30. The front portion 22 includes two front corner portions 32 which include front connectors. The rear portion 26 includes two rear corner portions 34 which include rear connectors which are complementary to the front connectors. The middle portion 24 includes a middle connector assembly located on a bottom surface 42 of the garment assembly 20. As shown in FIG. 3, a quantity of connector material 33 extends between the front corner portions 32 of the front portion 22 of the garment assembly 20.

Figure 2:
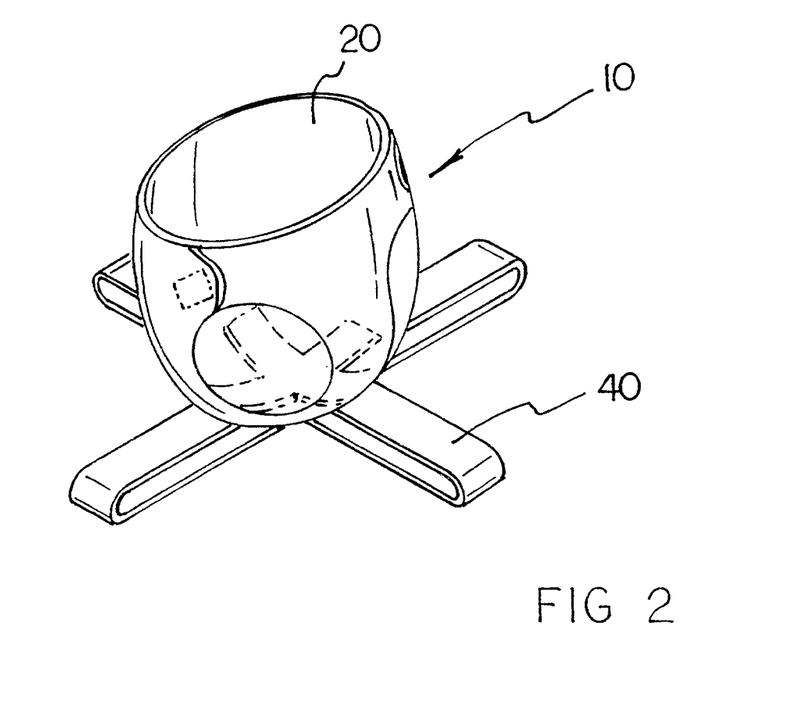
FIG. 2 is an enlarged perspective view of the embodiment of the garment-type personnel restraint apparatus shown in FIG. 1 in an orientation for connection to a seat.

The strap assembly 40 includes a strap connection assembly adapted to connect to the middle connector assembly of the garment assembly 20. The strap assembly 40 includes one strap portion 52 which has a sufficient strap length 54 for encompassing the seat portion 16 of the chair 14. The strap portion 52 includes a first end connector 56 and a second end connector 58 adapted to connect with each other when the strap portion 52 encompasses the seat portion 16 of the chair 14.

The front connectors includes first hook or loop connectors 36, and the complementary rear connectors includes second loop or hook connectors 38 to the first hook or loop connectors 36. The middle connector assembly includes a quantity of middle-connector hook or loop connectors 48, and the strap connection assembly includes a quantity of strap-connector loop or hook connectors 46 which are complementary to the middle-connector hook or loop connectors 48.

The strap assembly 40 includes a second strap portion 60 connected at right angles to the strap portion 52. The second strap portion 60 has a sufficient strap length 62 for encompassing the seat portion 16 of the chair 14. The second strap portion 60 includes a first end connector 66 and a second end connector 68 adapted to connect with each other when the second strap portion 60 encompasses the seat portion 16 of the chair 14. The hook or loop connectors and complementary loop or hook connectors can be made from well known VELCRO™ material.

Figure 1:
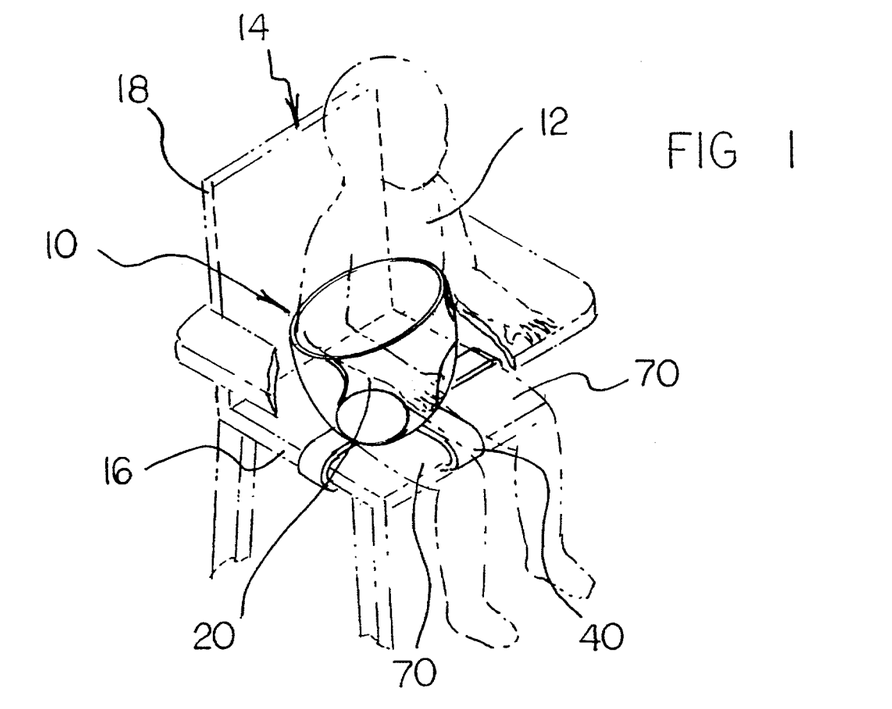
FIG. 1 is a perspective view showing a first embodiment of the garment-type personnel restraint apparatus of the invention worn by a child seated in a high chair.

In using the embodiment of the invention shown in FIGS. 1–4, a strap assembly 40 is first placed on the seat portion 16 of the chair 14 so that the strap-connector loop or hook connectors 46 face upward. In FIG. 1, the chair 14 is a high chair and the person 12 sitting in the high chair is a child. Then, the first strap portion 52 is wrapped around the seat portion 16 to encompass it in one direction. Then the first end connector 56 and the second end connector 58 are fastened together to secure the first strap portion 52 onto the seat portion 16. Then the second strap portion 60 is wrapped around the seat portion 16 at right angles to the first strap portion 52. Then the third connector assembly 66 and the fourth connector assembly 68 are fastened together to more firmly secure the second strap portion 60 onto the seat portion 16. Then, the garment assembly 20, in an unfolded condition, is placed on the strap assembly 40 so that the middle-connector hook or loop connectors 48 of the middle connector assembly of the garment assembly 20 are placed in registration with the strap-connector loop or hook connectors 46 of the strap assembly 40. In this way, the garment assembly 20 is secured to the strap assembly 40 which has already been secured to the seat portion 16 of the chair 14.

Then, a person 12 sits on the middle portion 24 of the garment assembly 20. The person's thighs 70 are placed adjacent to the middle portion 24 of the garment assembly 20, and the front corner portions 32 of the front portion 22 of the garment assembly 20 are lifted up so that the person's thighs 70 straddle some of the front portion 22 of the garment assembly 20. Then, the rear corner portions 34 of the rear portion 26 of the garment assembly 20 are lifted up. The second loop or hook connectors 38 are placed in connection with the first hook or loop connectors 36, whereby the garment assembly 20 forms legless pants for the person. The connection between the middle-connector hook or loop connectors 48 of the garment assembly 20 and the strap-connector loop or hook connectors 46 of the strap assembly 40 prevents the person 12 from sliding off of the seat portion 16 of the chair 14. To remove the person from the garment-type personnel restraint apparatus 10 of the invention, the steps described above are carried out in reverse.

Alternatively, the strap assembly 40 can be installed on the seat portion 16 of the high chair, and the garment assembly 20 can be installed on the child. Then, the child, who is wearing the garment assembly 20, can be seated on the seat portion 16 of the chair 14. Thereby, the middle-connector hook or loop connectors 48 of the garment assembly 20 will engage the strap-connector loop or hook connectors 46 of the strap assembly 40 for securing the child in the high chair.

Turning to FIGS. 5–8, a second embodiment of the invention is shown. Reference numerals are shown that correspond to like reference numerals that designate like elements shown in the other figures. In addition, the front portion 22 of the garment assembly 20 includes a two-strap belt assembly 72 adapted to encircle a person's waist. The two-strap belt assembly 72 includes a first end connector 74 and a second end connector 76 adapted to connect together when the two-strap belt assembly 72 encircles the person's waist. The rear portion 26 of the garment assembly 20 includes a back-covering portion 27 connected to the middle portion 24 of the garment assembly 20. A shoulder-covering portion 29 is connected to the back-coveting portion 27, and a torso-covering portion 31 is connected to the shoulder-coveting portion 29. The back-covering portion 27 of the rear portion 26 of the garment assembly 20 includes a back-located connector assembly 78 located on an outer surface of the back-covering portion 27. The shoulder-covering portion 29 of the rear portion 26 of the garment assembly 20 includes an aperture 80 adapted to fit over a head 82 and a neck 84 of a person and includes shoulder strap portions 86 adjacent to the aperture 80, and the torso-covering portion 31 includes an apron portion 88 and strap assemblies 90 which extend laterally from the apron portion 88. The strap assemblies 90 include strap connectors 92 that are adapted to connect with complementary receiver connectors 94 that are located on the back-covering portion 27 of the rear portion 26 of the garment assembly 20.

In FIGS. 5–8, the strap assembly 40 includes a strap array for encompassing the back portion 18 of the chair 14. A back-covering portion 96 is connected between the strap array, and a back-covering-portion-mounted connector assembly 98 located on the back-covering portion 96 adapted for connection to the back-located connector assembly 78 of the garment assembly 20. The strap array includes a front portion 43, a middle portion 45 connected to the front portion 43, and a rear portion 47 connected to the middle portion 45. The front portion 43 of the strap array includes a plurality of strap assemblies 41 which project laterally from the front portion 43. The strap assemblies 41 include connector-carrying ends 49. The rear portion 47 of the strap array includes connector portions 51 which are complementary to the connector-carrying ends 49 of the strap assemblies 41.

In using the embodiment of the invention shown in FIGS. 5–8, the garment assembly 20 is first laid out on a flat surface. An adult person sits upon the middle portion 24 of the garment assembly 20 facing toward the front portion 22 of the garment assembly 20. The apron portion 88 of the garment assembly 20 is grasped and pulled over the person so that the person's head fits through the aperture 80, so that the back-coveting portion 27 of the rear portion 26 of the garment assembly 20 rests upon the person's back, so that the shoulder-covering portion 29 of the rear portion 26 of the garment assembly 20 fits over the person's shoulders, and so that the torso-covering portion 31 of the rear portion 26 of the garment assembly 20 covers the person's torso. Then, the two-strap belt assembly 72 is pulled up the front of the person, and the two-strap belt assembly 72 is moved to encircle the person's waist. Then, the first end connector 74 of the two-strap belt assembly 72 is connected to the second end connector 76 of the two-strap belt assembly 72 to secure the front portion 22 of the garment assembly 20 to the person. Then, the strap connectors 92 of the strap assemblies 90 are connected to the receiver connectors 94 of the back-covering portion 27 for securing the apron portion 88 to the front of the torso and for securing the back-covering portion 27 to the back of the torso. At this point, the garment assembly 20 is fully in position on the person. In this position, the back-located connector assembly 78 of the garment assembly 20 faces backward as the garment assembly 20 is worn by the person. Additional connectors 53 and 55 can be employed to connect a top edge of the front portion 22 to a bottom edge of the apron portion 88.

Figures 5, 6:
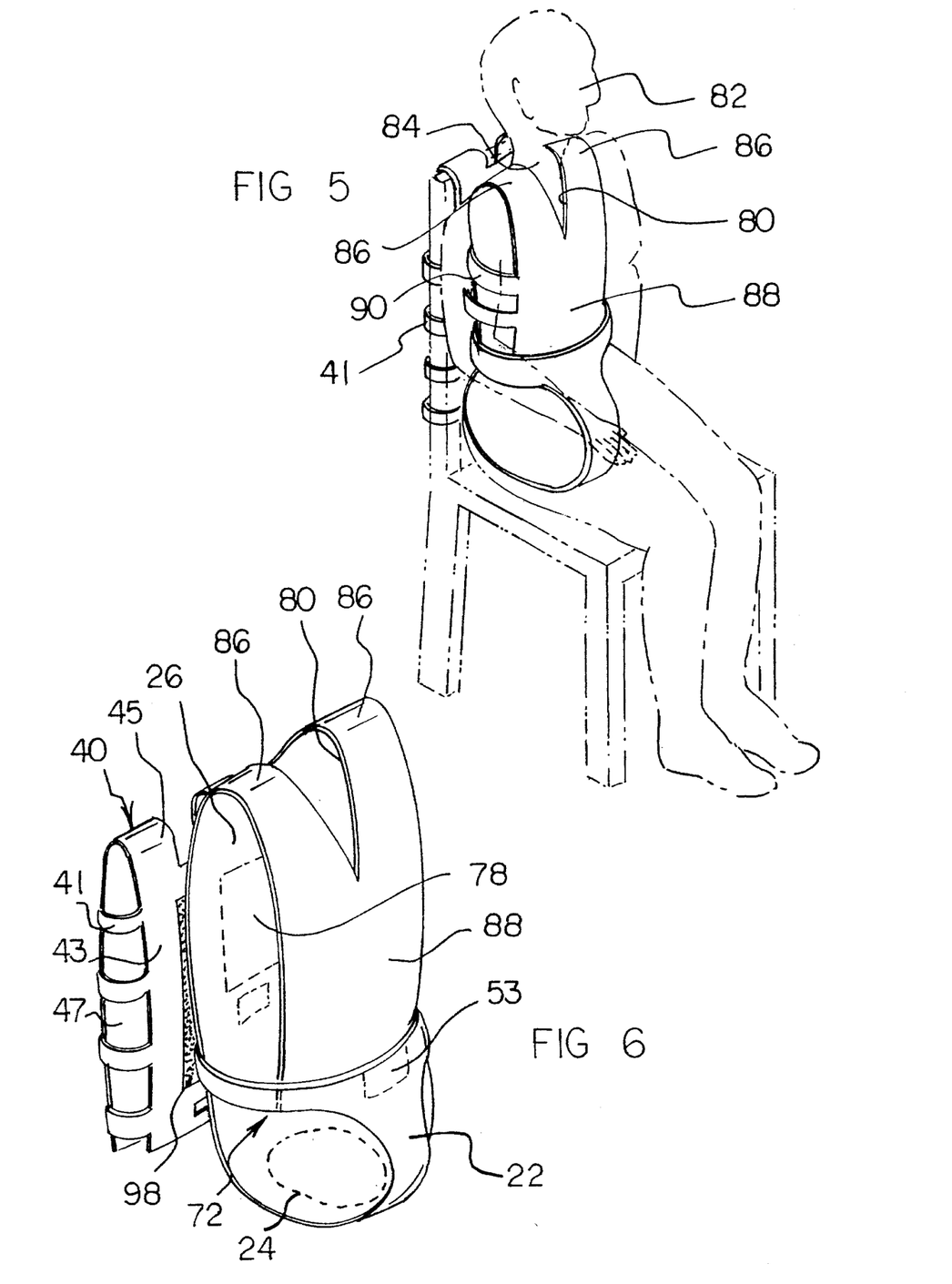
FIG. 5 is a perspective view showing a second embodiment of the garment-type personnel restraint apparatus of the invention worn by an adult seated in a conventional chair.
FIG. 6 is an enlarged perspective view of the embodiment of the garment-type personnel restraint apparatus shown in FIG. 5 in an orientation for connection to a vertical back portion of a chair.
Figures 7, 8:
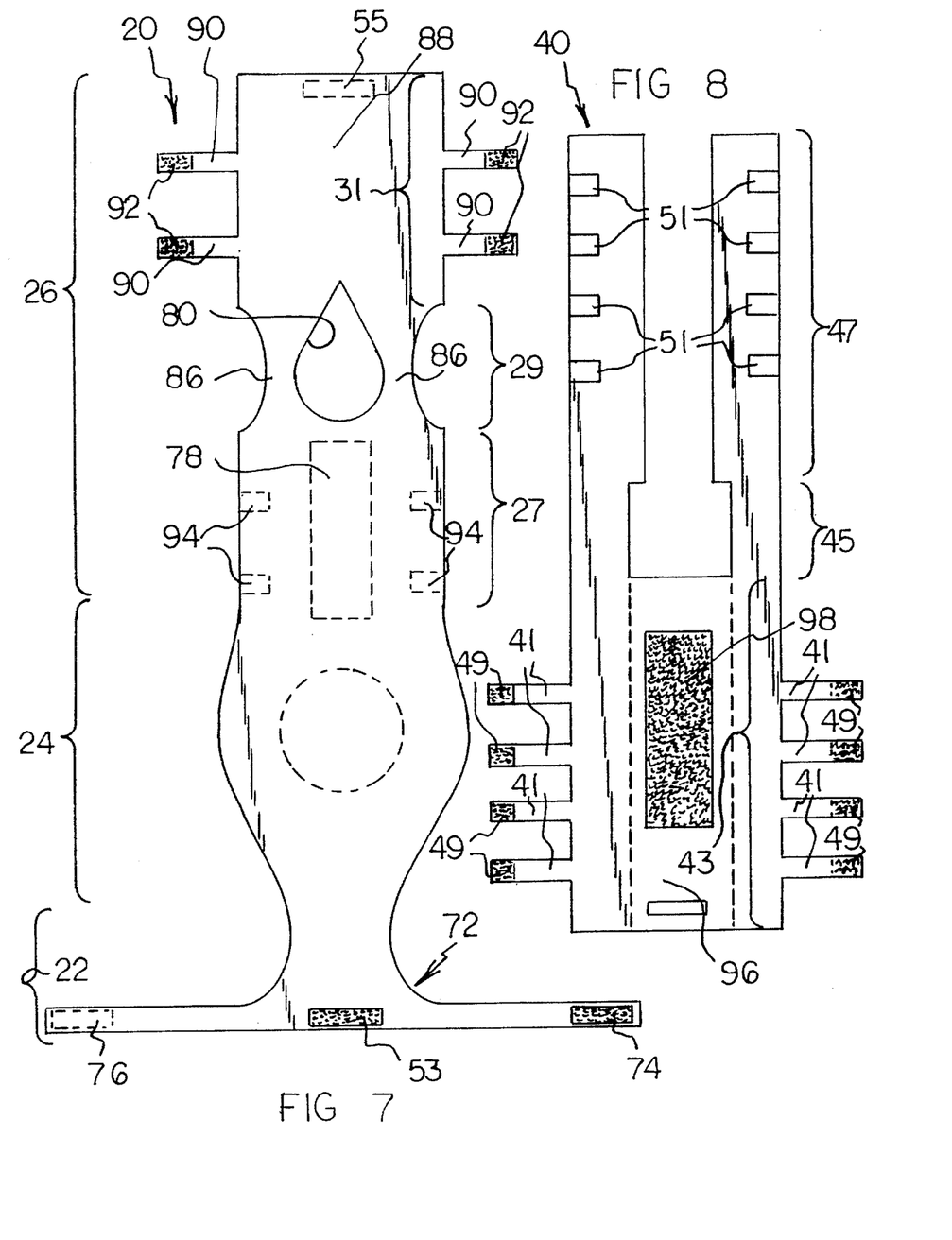
FIG. 7 is a top view of a vest and pants portion of the embodiment of the invention shown in FIG. 5 with the vest and pants portion in a flat, open orientation.
FIG. 8 is a bottom view of a seat-back-engaging portion of the embodiment of the invention shown in FIG. 5 with the seat-back-engaging portion in a flat, open orientation.

The strap assembly 40 is installed on the back portion 18 of a conventional chair 14. To do so, the back-covering portion 96 of the strap assembly 40 is draped over the front side of the back portion 18 of the chair 14. The middle portion 45 of the strap assembly 40 rests upon the topmost edge of the back portion 18 of the chair 14, and the rear portion 47 of the strap assembly 40 is adjacent to the rear side of the back portion 18 of the chair 14. Then, the strap assemblies 41 are wrapped around the sidemost edges of the back portion 18 of the chair 14, and the connector-carrying ends 49 of the strap assemblies 41 are connected to the connector portions 51 of the rear portion 47 of the strap assembly 40. In this way, the strap assembly 40 is secured to the back portion 18 of the chair 14. Moreover, the back-covering-portion-mounted connector assembly 98 faces forward.

Now, with the back-located connector assembly 78 of the garment assembly 20 facing backward when worn on a person, and with the back-covering-portion-mounted connector assembly 98 of the strap assembly 40 facing forward when the strap assembly 40 is installed on the back portion 18 of the chair 14, when the person sits on the seat portion 16 of the chair 14 and leans backward, the back-located connector assembly 78 interconnects with the back-covering-portion-mounted connector assembly 98, thereby securing the person to the chair 14 by of the interconnected garment assembly 20 and strap assembly 40.

All of the following connectors can be made from VEL-CRO™ hook or loop connector materials the connector-carrying ends 49 of the strap assemblies 41, the connector portions 51 of the rear portion 47 of the strap assembly 40, the first end connector 74 of the two-strap belt assembly 72, the second end connector 76 of the two-strap belt assembly 72, the strap connectors 92 of the strap assemblies 90 of the torso-covering portion 31 of the rear portion 26 of the garment assembly 20, the receiver connectors 94 of the back-covering portion 27 of the rear portion 26 of the garment assembly 20, and the connectors 53 and 55.

The components of the garment-type personnel restraint apparatus of the invention can be made from inexpensive and durable cloth and plastic materials. Preferably, both the garment assembly and the strap assembly 40 are machine washable.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved garment-type personnel restraint apparatus that is low in cost, relatively simple in design and operation, and which does not impede a child's leg movement when the child is seated in a high chair. With the invention, a garment-type personnel restraint apparatus is provided which does not employ wood. With the invention, a garment-type personnel restraint apparatus is provided which enables a child to be removed from the seat of a high chair with a two-handed operation. With the invention, a garment-type personnel restraint apparatus provides an apron-like portion for protecting a person's chest from materials that soil clothing. With the invention, a garment-type personnel restraint apparatus is provided which has a portion for connecting the person's torso to the vertically oriented back of a chair.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as encompass all such modifications as well as all relationships equivalent to those illustrated in the drawings and described in the specification.

Finally, it will be appreciated that the purpose of the foregoing Abstract provided at the beginning of this specification is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A garment-type personnel restraint apparatus for securing a person to a chair which has a seat portion and a back portion extending upward from the seat portion, comprising:

a garment assembly adapted to be worn by the person, wherein said garment assembly includes a front portion, a middle portion, and a rear portion, wherein said garment assembly includes a connector assembly located on an outer surface of said garment assembly, and a strap assembly which includes a strap connection assembly adapted to connect to said outer-surface garment connector assembly and which includes a strap array which encompasses either the seat portion or the back portion of the chair, wherein said front portion and said rear portion of said garment assembly have at least a first width, said middle portion has a second width, said first width is greater than said second width, said front portion includes two front corner portions which include front connectors, said rear portion includes two rear corner portions which include rear connectors which are complementary to said front connectors, and said middle portion includes a middle connector assembly located on a bottom surface of said garment assembly, and wherein said middle connector assembly includes a quantity of middle-connector hook or loop connectors and said strap connection assembly includes a quantity of strap-connector loop or hook connectors which are complementary to said middle-connector hook or loop connectors.

2. The apparatus of claim 1 wherein said strap array of said strap assembly includes at least one strap portion which has a sufficient strap length for encompassing either the seat portion or the back portion of the chair, wherein said at least one strap portion includes a first end connector and a second end connector adapted to connect with each other when said at least one strap portion encompasses either the seat portion or the back portion of the chair.

3. The apparatus of claim 2 wherein said strap assembly includes a second strap portion connected at right angles to said strap portion, wherein said second strap portion has a sufficient strap length for encompassing the seat portion of the chair, wherein said second strap portion includes a first end connector and a second end connector adapted to connect with each other when said second strap portion encompasses the seat portion of the chair.

4. The apparatus of claim 1 wherein:

said strap assembly which includes a strap connection assembly adapted to connect to said middle connector assembly of said garment assembly, said strap assembly includes at least one strap portion which has a sufficient strap length for encompassing the seat portion of the chair, and said at least one strap portion includes a first end connector and a second end connector adapted to connect with each other when said at least one strap portion encompasses the seat portion of the chair.

5. The apparatus of claim 1 wherein:

said front connectors include first hook or loop connectors, and said complementary rear connectors include second loop or hook connectors to said first hook or loop connectors.

6. A garment-type personnel restraint apparatus for securing a person to a chair which has a seat portion and a back portion extending upward from the seat portion, comprising:

a garment assembly adapted to be worn by the person, wherein said garment assembly includes a front portion, a middle portion, and a rear portion, wherein said garment assembly includes a connector assembly located on an outer surface of said garment assembly, and a strap assembly which includes a strap connection assembly adapted to connect to said outer-surface garment connector assembly and which includes a strap array which encompasses either the seat portion or the back portion of the chair wherein said front portion of said garment assembly includes a two-strap belt assembly adapted to encircle a person's waist, wherein said two-strap belt assembly includes a first end connector and a second end connector adapted to connect together when said two-strap belt assembly encircles the person's waist, wherein said rear portion of said garment assembly includes a back-covering portion connected to said middle portion of said garment assembly, a shoulder-covering portion connected to said back-covering portion, and a torso-covering portion connected to said shoulder-covering portion, wherein said back-covering portion of said rear portion of said garment assembly includes a back-located connector assembly located on an outer surface of said back-covering portion, wherein said shoulder-covering portion of said rear portion of said garment assembly includes an aperture adapted to fit over a head and a neck of a person and includes shoulder strap portions adjacent to said aperture, wherein said torso-covering portion includes an apron portion and strap assemblies which extend laterally from said apron portion, and wherein said strap assemblies include strap connectors that are adapted to connect with complementary receiver connectors that are located on said back-covering portion of said rear portion of said garment assembly.

7. The apparatus of claim 6 wherein said strap assembly includes:

a strap array for encompassing the back portion of the chair, a back-covering portion connected between said strap array, and a back-covering-portion-mounted connector assembly located on said back-covering portion adapted for connection to said back-located connector assembly of said garment assembly.

8. The apparatus of claim 7 wherein said strap array includes a front portion, a middle portion connected to said front portion, and a rear portion connected to said middle portion.

9. The apparatus of claim 8 wherein:

said front portion of said strap array includes a plurality of strap assemblies which project laterally from said front portion, said strap assemblies include connector-carrying ends, said rear portion of said strap array includes connector portions which are complementary to said connector-carrying ends of said strap assemblies.

\* \* \* \* \*